United States Patent
Thanki et al.

(10) Patent No.: US 6,320,056 B1
(45) Date of Patent: Nov. 20, 2001

(54) PROCESS FOR THE PREPARATION OF BROMO-FUNCTIONALIZED BENZOTRIAZOLE UV ABSORBERS

(75) Inventors: Paragkumar Nathalal Thanki; Raj Pal Singh, both of Pune (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 09/749,277

(22) Filed: Dec. 27, 2000

(51) Int. Cl.$^7$ .................................................. C07D 249/20
(52) U.S. Cl. .............................................. 548/259; 548/260
(58) Field of Search ...................................... 548/259, 260

(56) References Cited

FOREIGN PATENT DOCUMENTS 63-92775 * 4/1988 (JP) .

OTHER PUBLICATIONS

Potacek et al., Chemical Abstracts, 95:7298, 1981.*

* cited by examiner

*Primary Examiner*—Fiona T. Powers
(74) *Attorney, Agent, or Firm*—Ladas & Parry

(57) ABSTRACT

The invention also pertains to a process for their preparation of bromo functionalised benzotriazole UV absorber of the general formula 1

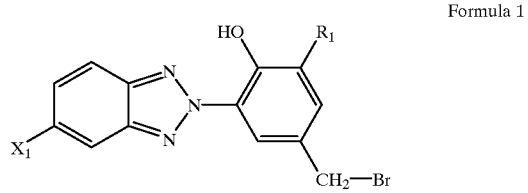

Formula 1 wherein $R_1$ is hydrogen, tert-butyl; $X_1$ is selected the group consisting of hydrogen, halogen, tert-butyl and $C_1$ to $C_{12}$ alkoxy by reacting a benzotriazole having formula 2

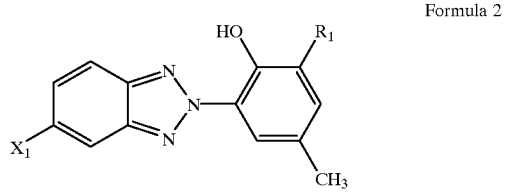

Formula 2 wherein $R_1$ is hydrogen, tert-butyl; $X_1$ is selected the group consisting of hydrogen, halogen, tert-butyl and $C_1$ to $C_{12}$ alkoxy with bromine in the presence of a free radical initiator in a non-polar solvent to produce a bromo functionialized benzotriazole.

3 Claims, No Drawings

PROCESS FOR THE PREPARATION OF BROMO-FUNCTIONALIZED BENZOTRIAZOLE UV ABSORBERS

FIELD OF THE INVENTION

This invention relates to a process for the preparation of bromo functionalised benzotriazole UV absorbers. More particularly the present invention relates to bromo-derivatives of benzotriazole UV absorbers having general formula 1

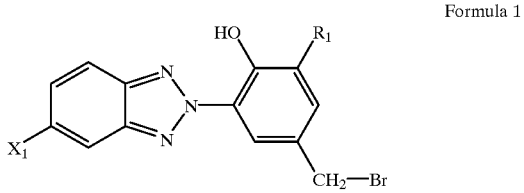

Formula 1 wherein $R_1$ is hydrogen, tert-butyl; $X_1$ is selected the group consisting of hydrogen, halogen, tert-butyl and $C_1$ to $C_{12}$ alkoxy. Still more particularly, the invention concerns the synthesis of intermediate compounds which are the bromo derivatives of conventional UV absorbers and useful for the synthesis of many other functional UV absorbers and a method for the preparation thereof.

Our copending application Ser. No. 09/749,274 now U.S. Pat. No. 6,284,895 filed on the same day as this application relates to the novel bromo functionalised benzotriazole UV absorbers obtained by the process of this invention.

BACKGROUND OF THE INVENTION

Most thermoplastic polymers and coating compositions are unstable to extended exposure to ultraviolet light source in atmosphere. Thermoplastics and coatings tend to demonstrate unwanted colour changes and reduced mechanical strength upon exposure to UV radiation. The preliminary effect of ultraviolet radiation on polymers is the formation of free radicals on the polymer chain, which react with atmospheric oxygen. This results in the formation of peroxide groups. Furthermore, decomposition of peroxide groups causes formation of carbonyl groups and chain scission. Irradiation in absence of oxygen causes the increase in crosslinking. Ultimately, this reflects on the mechanical properties and the colour of the polymeric materials. In order to prevent or at least retard the damage caused by these factors, stabilizers are added to the plastics.

UV absorbers are compounds that upon addition to the polymers are capable of preventing or retarding the reactions of degradation caused by light energy. 2-Hydroxyphenyl benzotriazoles are one of the most important UV absorbers, which are used commercially. The preparation and use of functional UV absorber in polymers and coatings is well documented.

In order to meet the need for the different UV absorbers for different systems, the reactive intermediates for the synthesis of novel UV absorber are very essential.

Side chain bromination in UV absorbers in the prior art is a three step reaction as reported in the literature [S.Yoshida & O.Vogl, Makromol.Chem.,183, 259(1982); S.Yoshida, C. P.Lillya & O. Vogl, Monatshefte Chem.,113, 603(1982); S.Yoshida, C. P.Lillya & O.Vogl, J.Polym.Sci., Polym.Chem.Ed., 20, 2215(1982)]. Literature reports the similar process via three-step reaction, which includes protection of hydroxyl group, bromination, and then deprotection reaction. However, there is no report of bromination of benzotriazole UV absorbers in the art.

Hydroxyphenyl benzotriazole monomers may be prepared by any method known in the art including those disclosed in U.S. Pat. Nos., 5,104,992, 4,943,637, and 5,097,041. 2-Aryl-2H-benzotriazoles monomers may be prepared by reducing o-nitroazobenzenes through a 2-phenylbenzotriazole-N-oxide intermediate. Reduction of o-nitroazobenzenes to 2-phenylbenzotriazole by zinc in presence of sodium hydroxide is disclosed in U.S. Pat. Nos. 3,018,269; 3,773,751; 4,041,044; and 4,224,451. Aldehyde reducing agents and aromatic ketone catalysts are disclosed in U.S. Pat. No. 4,835,284. All of these patents are incorporated herein by reference.

It is therefore important to obtain bromo functionalized UV absorber is highly reactive and can be used for the synthesis of various functional UV absorbers.

OBJECTS OF THE INVENTION

The object of the present invention is therefore to provide a process for the preparation of bromo-functionialized benzotriazole UV absorbers.

SUMMARY OF THE INVENTION

Accordingly the present invention provides a process for preparation of bromo-functionalized benzotriazole IJV absorbers having a general formula 1

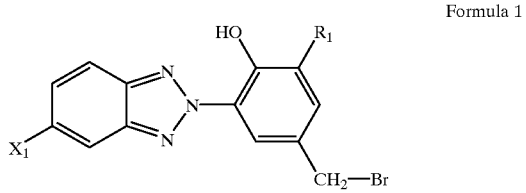

Formula 1 wherein $R_1$ is selected from hydrogen and tert-butyl; $X_1$ is selected the group consisting of hydrogen, halogen, tert-butyl and $C_1$ to $C_{12}$ alkoxy, by reacting a benzotriazole of the formula 2

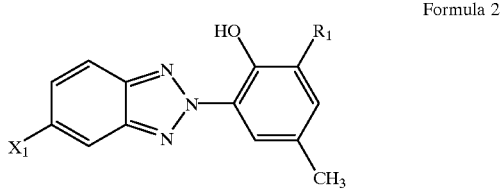

Formula 2 wherein $R_1$ is selected from hydrogen and tert-butyl; $X_1$ is selected the group consisting of hydrogen, halogen, tert-butyl and $C_1$ to $C_{12}$ alkoxy, with bromine in presence of a non-polar solvent and a free radical initiator at a temperature ranging between 45 to 52° C. for a period of 4 to 10 hours, bringing the reaction mixture to ambient temperature, separating the solvent and purifying the product by recrystallization to obtain the pure product.

In one embodiment of the invention, the non-polar solvent used is selected from the group consisting of carbon tetrachloride, benzene, n-pentane, 1,2-dichloroethane, 1,2-dibromoethane, chloro and bromo substituted benzenes.

In another embodiment of the invention, the free radical initiator is selected from the group consisting of 2,2'-azobisisobutyronitrile, 1,1'-azobis-2-cyclopropylpropionitrile, 2,2'-azobis-2-cyclopropylpropionitrile, 2,2'-azobis-2,4,4-trimethylvalaronitrile, 1,1'-azobis-1 cyclooctanenitrile, azo-bis-(1-carbomethoxy-3-methylpropane).

In another embodiment of the invention the recrystallisation is carried out using solvents such as acetone, methyl ethyl ketone, chloroform.

DETAILED DESCRIPTION OF THE INVENTION

The process of the present invention begins with a benzotriazole monomer of the formula 2:

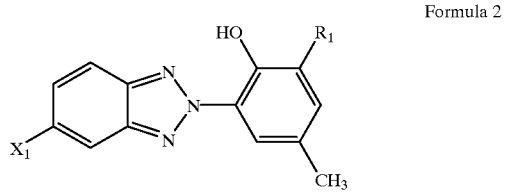

Formula 2 wherein $R_1$ is hydrogen, tert-butyl; $X_1$ is selected the group consisting of hydrogen, halogen, tert-butyl and $C_1$ to $C_{12}$ alkoxy.

Hydroxyphenyl benzotriazole monomers may be prepared by any method known in the art including those disclosed in U.S. Pat. Nos., 5,104,992; 4,943,637; and 5,097,041. 2-Aryl-2H-benzotriazoles monomers may be prepared by reducing o-nitroazobenizenes through a 2-phenylbenzotriazole-N-oxide intermediate. Reduction of o-nitroazobenzenes to 2-phenylbenzotriazole by zinc in presence of sodium hydroxide is disclosed in U.S. Pat. Nos. 3,018,269; 3,773,751; 4,041,044; and 4,224,451. Aldehyde reducing agents and aromatic ketone catalysts are disclosed in U.S. Pat. No. 4,835,284. All of these patents are incorporated herein by reference.

Brominiation of p-cresol in the same condition did not proceed whereas in the case of benzotriazole UV absorbers, same reaction gives the brominated product with bromination at methyl side chain in very high yield.

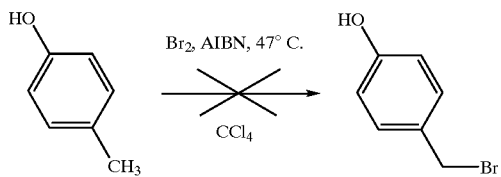

The process of the present invention is described hereinbelow with reference to examples, which are illustrative only and should not be construed to limit the scope of the present invention in any manner.

EXAMPLE 1
Synthesis of 2-(2H-Benzotriazole-2-yl)-4-bromomethylphenol 2-(2H-Benzotriazole-2-yl)-4-bromomethylphenol was prepared from the bromination of 2-(2H-Benzotriazole-2-yl)-4-methylphenol using azobis isobutyronitrile (AIBN) as an initiator. In a 500 ml three-necked round bottomed flask, 5 g (0.0223 mol) of 2-(2H-Benzotriazole-2-yl)-4-methylphenol and 100 mg of AIBN were taken and dissolved in 150 ml of dry carbon tetrachloride. In a separate conical flask 4.18 g (1.5 ml, 0.03 mol) of bromine was dissolved in 75 ml of dry carbon tetrachloride and solution was transferred to a cylindrical funnel with pressure equalizing tube. Three-necked round-bottomed flask containing solution of 2-(2H-Benzotriazole-2-yl)-4-methylphenol was kept in oil-bath with temperature 47° C. Nitrogen was bubbled through the solution for creating inert atmosphere. Cylindrical funnel containing bromine solution was mounted on the three-necked round-bottomed flask. Solution in the flask was continuously stirred with the help of magnetic stirrer. Bromine solution was added, drop-by-drop, from funnel to the flask for a span of 4–5 hours till all the solution was poured out. After that heating was stopped and the final reaction mixture was allowed to cool at room temperature. Product was separated by solvent evaporation. Finally the product was purified by recrystallization from acetone. The yield of 2-(2H-Benzotriazole-2-yl)-4-bromomethylphenol was 5.5 g (80%).

EXAMPLE 2
Synthesis of 2-(2'-hydroxy-3'-tert-butyl-5'-bromomethyphenyl)-5-chlorobenzotriazole 2-(2'-hydroxy-3'-tert-butyl-5'-bromomethyphenyl)-5-chlorobenzotriazole was prepared from the bromination of 2-(2'-hydroxy-3'-tert-butyl-5'-methyphenyl)-5-chlorobenzotriazole using azobis isobutyronitrile (AIBN) as an initiator. In a 500 ml three-necked round bottomed flask, 7.042 g (0.0223 mol) 2-(2'-hydroxy-3'-tert-butyl-5'-methyphenyl)-5-chlorobenzotriazole and 100 mg of AIBN were taken and dissolved in 150 ml of dry carbon tetrachloride. In a separate conical flask 4.18 g (1.5 ml, 0.03 mol) of bromine was dissolved in 75 ml of dry carbon tetrachloride and solution was transferred to a cylindrical funnel with pressure equalizing tube. Three-necked round-bottomed flask containing solution of 2-(2'-hydroxy-3'-tert-butyl-5'-methyphenyl)-5-chlorobenzotriazole was kept in oil-bath with temperature 50° C. Nitrogen was bubbled through the solution for creating inert atmosphere. Cylindrical funnel containing bromine solution was mounted on the three-necked round-bottomed flask. Solution in the flask was continuously stirred with the help of magnetic stirrer. Bromine solution was added, drop-by-drop from funnel to the flask for a span of 4–5 hours till all the solution was poured out. After that heating was stopped and the final reaction mixture was allowed to cool at room temperature. Product was separated by solvent evaporation. Finally the product was purified by recrystallization from acetone. The yield of 2-(2'-hydroxy3'-tert-butyl-5'-bromomethyphenyl)-5-chlorobenzotriazole was 7.2 g (81%).

EXAMPLE 3
Synthesis of 2-(2'-hydroxy-3'-tert-butyl-5'-bromomethyphenyl)benzotriazole 2-(2'-hydroxy-3'-tert-butyl-5'-bromomethyphenyl) benzotriazole was prepared from the bromination of 2-(2'-hydroxy-3'-tert-butyl-5'-methyphenyl)benzotriazole using azobis isobutyronitrile (AIBN) as an initiator. In a 500 ml three-necked round bottomed flask, 6.274 g (0.0223 mol) 2-(2'-hydroxy-3'-tert-butyl-5'-methyphenyl)benzotriazole and 100 mg of AIBN were taken and dissolved in 150 ml of dry carbon tetrachloride. In a separate conical flask 4.18 g (1.5 ml, 0.03 mol) of bromine was dissolved in 75 ml of dry carbon tetrachloride and solution was transferred to a cylindrical funnel with pressure equalizing tube. Three-necked round-bottomed flask containing solution of 2-(2'-hydroxy-3'-tert-butyl-5'-methyphenyl)benzotriazole was kept in oil-bath with temperature 50° C. Nitrogen was bubbled through the solution for creating inert atmosphere. Cylindrical funnel containing bromine solution was mounted on the three-necked round-bottomed flask. Solution in the flask was continuously stirred with the help of magnetic stirrer. Bromine solution was added, drop-by-drop, from funnel to the flask for a span of 4–5 hours till all the solution was poured out. After that heating was stopped and the final reaction mixture was allowed to cool at room temperature. Product was separated by solvent evaporation. Finally the product was purified by recrystallization from acetone. The yield of 2-(2'-hydroxy-3'-tert-butyl-5'-bromomethyphenyl) benizotriazole was 6.6 g (82%)

EXAMPLE 4

Synthesis of 2-(2'-hydroxy-5'-bromomethyphenyl)-5-tert-butylbenzotriazole 2-(2'-hydroxy-5'-bromomethyphenyl)-5-tert-butylbenzotriazole was prepared from the bromination of 2-(2'-hydroxy-5'-methyphenyl)-5-tert-butylbenzotriazole using azobis isobutyronitrile (AIBN) as an initiator. In a 500 ml three-necked round bottomed flask, 6.274 g (0.0223 mol) 2-(2'-hydroxy-5'-methyphenyl)-5-tert-butylbenzotriazole and 100 mg of AIBN were taken and dissolved in 150 ml of dry carbon tetrachloride. In a separate conical flask 4.18 g (1.5 ml, 0.03 mol) of bromine was dissolved in 75 ml of dry carbon tetrachloride and solution was transferred to a cylindrical funnel with pressure equalizing tube. Three-necked round-bottomed flask containing solution of 2-(2'-hydroxy-5'-methyphenyl)-5-tert-butylbenzotriazole was kept in oil-bath with temperature 50° C. Nitrogen was bubbled through the solution for creating inert atmosphere. Cylindrical funnel containing bromine solution was mounted on the three-necked round-bottomed flask. Solution in the flask was continuously stirred with the help of magnetic stirrer. Bromine solution was added, drop-by-drop, from funnel to the flask for a span of 4–5 hours till all the solution was poured out. After that heating was stopped and the final reaction mixture was allowed to cool at room temperature. Product was separated by solvent evaporation. Finally the product was purified by recrystallization from acetone. The yield of 2-(2'-hydroxy-5'-bromomethyphenyl)-5-tert-butylbenzotriazole was 6.8 g (84%)

EXAMPLE 5

Synthesis of 2-(2'-hydroxy-5'-bromomethyphenyl)-5-ethoxy benzotriazole 2-(2'-hydroxy-5'-bromomethyphenyl)-5-ethoxybenzotriazole was prepared from the brominiation of 2-(2'-hydroxy-5'-methyphenyl)-5-ethoxybenzotriazole using azobis isobutyronitrile (AIBN) as an initiator. In a 500 ml three-necked round bottomed flask, 6.275 g (0.0223 mol) 2-(2'-hydroxy-5'-methyphenyl)-5-ethoxybenzotriazole and 100 mg of AIBN were taken and dissolved in 150 ml of dry carbon tetrachloride. In a separate conical flask 4.18 g (1.5 ml, 0.03 mol) of bromine was dissolved in 75 ml of dry carbon tetrachloride and solution was transferred to a cylindrical funnel with pressure equalizing tube. Three-necked round-bottomed flask containing solution of 2-(2'-hydroxy-5'-methyphenyl)-5-ethoxybenzotriazole was kept in oil-bath with temperature 50° C. Nitrogen was bubbled through the solution for creating inert atmosphere. Cylindrical funnel containing bromine solution was mounted on the three-necked round-bottomed flask. Solution in the flask was continuously stirred with the help of magnetic stirrer. Bromine solution was added, drop-by-drop, from funnel to the flask for a span of 4–5 hours till all the solution was poured out. After that heating was stopped and the final reaction mixture was allowed to cool at room temperature. Product was separated by solvent evaporation. Finally the product was purified by recrystallization from acetone. The yield of 2-(2'-hydroxy-5'-bromomethyphenyl)-5-ethoxybenzotriazole was 6.6 g (85%)

EXAMPLE 6

Synthesis of 2-(2'-hydroxy-5'-bromomethyphenyl)-5-tert-octyloxybenzotriazole 2-(2'-hydroxy-5'-bromomethyphenyl)-5-tert-octyloxybenzotriazole was prepared from the bromination of 2-(2'-hydroxy-5'-methyphenyl)-5-tert-octyloxybenzotriazole using azobis isobutyronitrile (AIBN) as an initiator. In a 500 ml three-necked round bottomed flask 8.236 g (0.0223 mol) 2-(2'-hydroxy-5'-methyphenyl)-5-tert-octyloxy benzotriazole and 100 mg of AIBN were taken and dissolved in 150 ml of dry carbon tetrachloride. In a separate conical flask 4.18 g (1.5 ml, 0.03 mol) of bromine was dissolved in 75 ml of dry carbon tetrachloride and solution was transferred to a cylindrical funnel with pressure equalizing tube. Three-necked round-bottomed flask containing solution of 2-(2'-hydroxy-5'-methyphenyl)-5-tert-octyloxybenzotriazole was kept in oil-bath with temperature 50° C. Nitrogen was bubbled through the solution for creating inert atmosphere. Cylindrical funnel containing bromine solution was mounted on the three-necked round-bottomed flask. Solution in the flask was continuously stirred with the help of magnetic stirrer. Bromine solution was added, drop-by-drop, from funnel to the flask for a span of 4–5 hours till all the solution was poured out. After that heating was stopped and the final reaction mixture was allowed to cool at room temperature. Product was separated by solvent evaporation. Finally the product was purified by recrystallization from acetone. The yield of 2-(2'-hydroxy-5'-bromomethyphenyl)-5-tert-octyloxybenzotriazole was 7.8 g (81%).

EXAMPLE 7

Synthesis of 2-(2'-hydroxy-5'-bromomethyphenyl)-5'-methoxybenzotriazole 2-(2'-hydroxy-5'-bromomethyphenyl)-5-methoxybenzotriazole was prepared from the bromination of 2-(2'-hydroxy-5'-methyphenyl)-5-methoxybenzotriazole using azobis isobutyronitrile (AIBN) as an initiator. In a 500 ml three-necked round bottomed flask, 5.693 g (0.0223 mol)2-(2'-hydroxy-5'-methyphenyl)-5-methoxybenzotriazole and 100 mg of AIBN were taken and dissolved in 150 ml of dry carbon tetrachloride. In a separate conical flask 4.18 g (1.5 ml, 0.03 mol) of bromine was dissolved in 75 ml of dry carbon tetrachloride and solution was transferred to a cylindrical funnel with pressure equalizing tube. Three-necked round-bottomed flask containing solution of 2-(2'-hydroxy-5'-methyphenyl)-5-methoxybenzotriazole was kept in oil-bath with temperature 50° C. Nitrogen was bubbled through the solution for creating inert atmosphere. Cylindrical funnel containing bromine solution was mounted on the three-necked round-bottomed flask. Solution in the flask was continuously stirred with the help of magnetic stirrer. Bromine solution was added, drop-by-drop, from tunnel to the flask for a span of 4–5 hours till all the solution was poured out. After that heating was stopped and the final reaction mixture was allowed to cool at room temperature. Product was separated by solvent evaporation. Finally the product was purified by recrystallization from acetone. The yield of 2-(2'-hydroxy-5'-bromomethyphenyl)-5-methoxybenzotriazole was 6.3 g (84%).

Our process has the edge over other processes by three strong points:

1) Our process is a single step process, whereas other similar processes are of three steps.
2) High yield (~80%) can be achieved very easily.
3) Reaction can be carried out via very facile route. Reaction conditions are very simple and moderate.

We claim:

1. A process for the preparation of bromo-functionalized benzotriazole UV absorber of formula 1

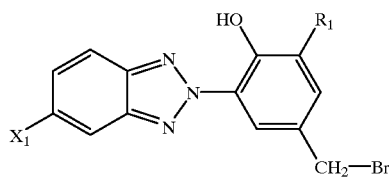

Formula 1 wherein $R_1$ is selected from hydrogen and tert-butyl; $X_1$ is selected from the group consisting of hydrogen, halogen, tert-butyl and $C_1$ to $C_{12}$ alkoxy, said process comprising reacting benzotriazole of formula 2

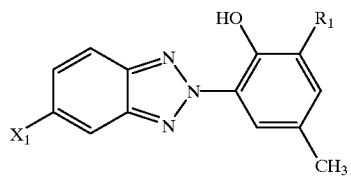

Formula 2 wherein $R_1$ is selected from hydrogen and tert-butyl; $X_1$ is selected the group consisting of hydrogen, halogen, tert-butyl and $C_1$ to $C_{12}$ alkoxy, with bromine in presence of a non-polar solvent and a free radical initiator selected from the group consisting of 2, 2'-azobisisobutyronitrile, 1,1'-azobis-2-cyclopropylpropionitrile, 2,2'-azobis-2-cyclopropylpropionitrile, 2,2'-azobis-2,4,4-trimethylvalaronitrile, 1,1'-azobis-1-cyclooctane-nitrile, and azo-bis-(1-carbomethoxy-3-methylpropane) at a temperature ranging between 45 to 52° C. for a period of 4 to 10 hours, bringing the reaction mixture to ambient temperature, separating the solvent and purifying the product by recrystallization.

2. The process as claimed in claim 1 wherein the non-polar solvent is selected from the group consisting of carbon tetrachloride, benzene, n-pentane, 1, 2-dichloroethane, 1,2-dibromoethane, chloro and bromo substituted benzenes.

3. The process as claimed in claim 1 wherein recrystallization is carried out using a solvent selected from the group consisting of acetone, methyl ethyl ketone and chloroform.

* * * * *